US00PP14034P39

(12) United States Plant Patent
Janick

(10) Patent No.: US PP14,034 P3
(45) Date of Patent: Jul. 29, 2003

(54) PEAR TREE NAMED 'P448-2'

(75) Inventor: Jules Janick, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/027,825

(22) Filed: Dec. 21, 2001

(65) Prior Publication Data

US 2003/0121086 P1 Jun. 26, 2003

(51) Int. Cl.[7] ..... A01H 5/00

(52) U.S. Cl. ..... Plt./176

(58) Field of Search ..... Plt./176

*Primary Examiner*—Bruce R. Campell
*Assistant Examiner*—Anne Marie Grünberg
(74) *Attorney, Agent, or Firm*—Klarquist Sparkman, LLP

(57) ABSTRACT

A variety of pear tree having a high productivity, tolerance to fireblight, consistently large fruit that ripens early, and fruit having a pleasant, juicy flavor.

1 Drawing Sheet

Latin name of the genus and species of the plant claimed: *Pyrus communis.*
Variety denomination: 'P448-2'.

BACKGROUND OF THE INVENTION

The present invention relates to a new and distinct variety of pear tree named 'P448-2'. My new tree resulted from a planned hybridization program and is a selection from crossing US386 (unpatented pear tree), as the seed parent and NJ 3 (unpatented pear tree released as 'Star' in 1968) as the pollen parent. The resulting tree was selected when growing in a cultivated area in Vincennes, Ind.

BRIEF SUMMARY OF THE INVENTION

The 'P448-2' variety is distinguished from other pear varieties due to the following unique combination of characteristics: high fruit productivity; consistent large fruit size; fruit which is juicy and has a pleasant flavor, even when crisp; fruit which ripens on the tree; and fruit which ripens early, observed to ripen in some years during the second week of August when grown in Vincennes, Ind.; and tolerance to fireblight.

NJ 3: Fruit size is above medium, pyriform, skin light green, flesh white, juicy, fine-grained but not buttery, quality good but internal breakdown observed in some seasons, ripens early (mid-August). Low resistance to fireblight.

US 386: Fruit size is medium, pyriform to ovate-pyriform, flesh creamy white to white, moderately juicy, moderately gritty, sweet to acidic but only fair quality, no aroma, none to light core breakdown, ripens early; (mid-August). Substantial resistance to fireblight.

Asexual reproduction of this new variety by budding and grafting onto Bartlett pear seedling (unpatented) rootstock shows that the foregoing characteristics come true to form, are firmly fixed and are established and transmitted through succeeding propagations. Asexual propagation of 'P448-2' was carried out at Purdue University, West Lafayette, Ind. and in New Salisbury, Ind.

The original tree and progeny have been observed growing in Vincennes, Ind. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWING

The accompanying illustration shows typical fruit and leaf specimens of this new pear variety.

The colors of an illustration of this type may vary with lighting conditions and, therefore, color characteristics of this new variety should be determined with reference to the observations described herein, rather than from this illustration alone.

DETAILED BOTANICAL DESCRIPTION

The following detailed description of the 'P448-2' variety is based on observations of asexually reproduced progeny. The observed progeny were trees which were about eleven years old growing on Bartlett pear seedling rootstock in Vincennes, Ind.

Scientific name: *Pyrus commmunis* 'P448-2'.
Parentage:
- *Seed parent.*—'US 386' (unpatented), which resulted from a cross between 'Mich US 437' (unpatented) and 'Re Carlos di Wurtemb' (unpatented).
- *Pollen parent.*—'NJ 3' (unpatented), which resulted from a cross between 'Beierschmidt' (unpatented) and 'NJ 1' (unpatented).

Tree:
- *Vigor.*—Moderate, but more vigorous than the 'Honeysweet' variety (U.S. Plant Pat. No. 4,379).
- *Overall shape.*—Upright, spreading.
- *Height.*—From about 14 to about 16 feet.
- *Width.*—Overall spread of about 12 feet.
- *Caliper.*—About 6 inches at about 4 inches above ground.

*Trunk*.—Slender to moderately stocky; stockier than 'Honeysweet,' but less stocky than 'Magness' (unpatented).

*Trunk bark texture*.—Scaly to slightly rough.

*Trunk bark color*.—Grey-brown (RHS 199A), not distinguished by patches or other markings.

*Primary branches*.—Upright growth habit, emerging from the trunk at about 30 to 40 degrees, with the angle of emergence increasing toward the top of the tree; no included bark has been observed to date; non-pubescent.

*Branch color*.—Both one-year old and two-year old branches are grey-orange (RHS 165B).

*Branch lenticels*.—Sparse, with a density of about 80 per square inch; oval and about 0.020 to 0.035 inch in size; grey-white (RHS 156D) in color.

*Internodes*.—Average internode length is 0.75 to 1.25 inches on a one-year old shoot.

*Hardiness*.—Zone 5.

*Disease resistance*.—Tolerant to fireblight, similar to the 'Honeysweet' variety; sensitive to Psylla species.

Leaves:

*Texture*.—Smooth, leathery.

*Sheen*.—Shiny.

*Length*.—About 2.6 inches to about 3.6 inches, averaging about 2.9 inches.

*Width*.—About 1.7 inches to about 2.1 inches, averaging about 1.9 inches.

*Thickness*.—About 0.003 inch to about 0.010 inch, averaging about 0.006 inch.

*Petiole*.—About 1.60 inches long, with a diameter of about 2.053 inches; yellow-green (RHS 153B) in color.

*Margin*.—Smooth to finely serrate.

*Tip shape*.—Acuminate.

*Stipules*.—Two in number with opposite arrangement; needle-shaped; about 0.066 inch in diameter; yellow-green (RHS 145A) in color.

*Leaf color*.—Upper leaf surface: green (RHS 137B). Lower leaf surface: grey-green (RHS 194A). Vein: yellow-green (RHS 154B).

*Pubescence*.—None.

The above length, width, thickness and other measurements were taken from observation of ten typical leaves in October of 2001.

Flowers:

*Shape*.—Oval.

*Size*.—Medium, approximately 29 mm in diameter.

*Color*.—Unopened bud: white (RHS 155D). Opened flower: white (RHS 155D).

*Petals*.—Five petals per flower and barely touching one another.

*Stamen*.—Twenty stamens per flower, about 4 to 5 mm long, and white in color.

*Arrangement*.—Single row.

*Anthers*.—General color red-purple; (RHS N74D).

*Pistil*.—Stigma: About 4–5 mm long. Styles: Five in number, fused at base; yellow-green (RHS 154A) in color.

*Sepals*.—About 3 mm long and about 3 mm wide; recurved; yellow-green (RHS 154A) in color; pubescent.

*Pollen*.—Yellow.

*Fragrance*.—Foul.

*Time of flower opening*.—Flower opening in 2001 in West Lafayette, Ind. was about April 17 and bloom peaked at April 23.

Fruit (observations from a limited number of fruit in August of 2001):

*Size*.—Large, typical fruit about 3.00 inches long and about 2.8 inches wide at the widest point.

*Shape*.—Oblong to ovate and symmetrical, with a typical length to diameter ratio of about 1.2; no ribbing or lobes on the calyx end of the fruit.

*Cavity*.—None.

*Basin*.—Shallow, about 0.2 inches deep and 0.76 inch wide; no pubescence.

*Stem*.—Long and stout; typically about 1.54 inches long and 0.14 inches in diameter; grey-orange (RHS 165A) in color.

*Locules*.—Five in number, closed, medium in size, and seeds are free from the carpel wall at maturity.

*Skin*.—Thin, fine, and russeted, with a moderately shiny finish and no tendency to become waxy or oily in storage.

*Lenticels*.—Inconspicuous; about 100 per square inch.

*Color*.—Yellow-green (RHS 145A) to green-yellow (RHS 1B). Overcolor: none. Russetting: some russetting present, predominantly at base.

*Fruit characteristics* (*based upon five fruits tested on about Aug. 2, 2001*).—Acid content: hard fruit has about 0.232 g/100 ml malic acid, while soft fruit has 0.250 g/100 ml malic acid. Firmness: about 5.7 to 8.2 kg, averaging about 7.3 kg. Soluble solids: about 11.0 to 11.8%, averaging about 11.45%. Starch index: on a scale of 1 (high starch) to 10 (low starch), range from 7 to 9, average 7.4. Flavor: Mild, sweet. Juiciness: moderate. Flesh color: yellow-white (RHS 158C). Aroma: slight.

*Core*.—Bundle area shape is basal, meeting, median; about 1.3 inches long and about 1.2 inches wide; calyx tube is closed and about 0.1 inches long; core lines are weakly defined.

*Seed*.—Typically 1 to 2 per cell; shape is acute at tip and round at base; about 0.33 inches long and 0.22 inches wide. Color is greyed-orange (RHS 166A).

*Fruit production*.—First picking date in 2001 was about August 6, and last picking date was about August 12; average production is 300 lbs. of fruit per tree.

*Storage*.—Fruit can be kept at room temperature for about one week and can be kept in cold storage (34° F.) for about two months.

*Usage*.—Eating, can be consumed crisp or soft.

I claim:

1. A new and distinct variety of pear tree, substantially as herein shown and described.

* * * * *

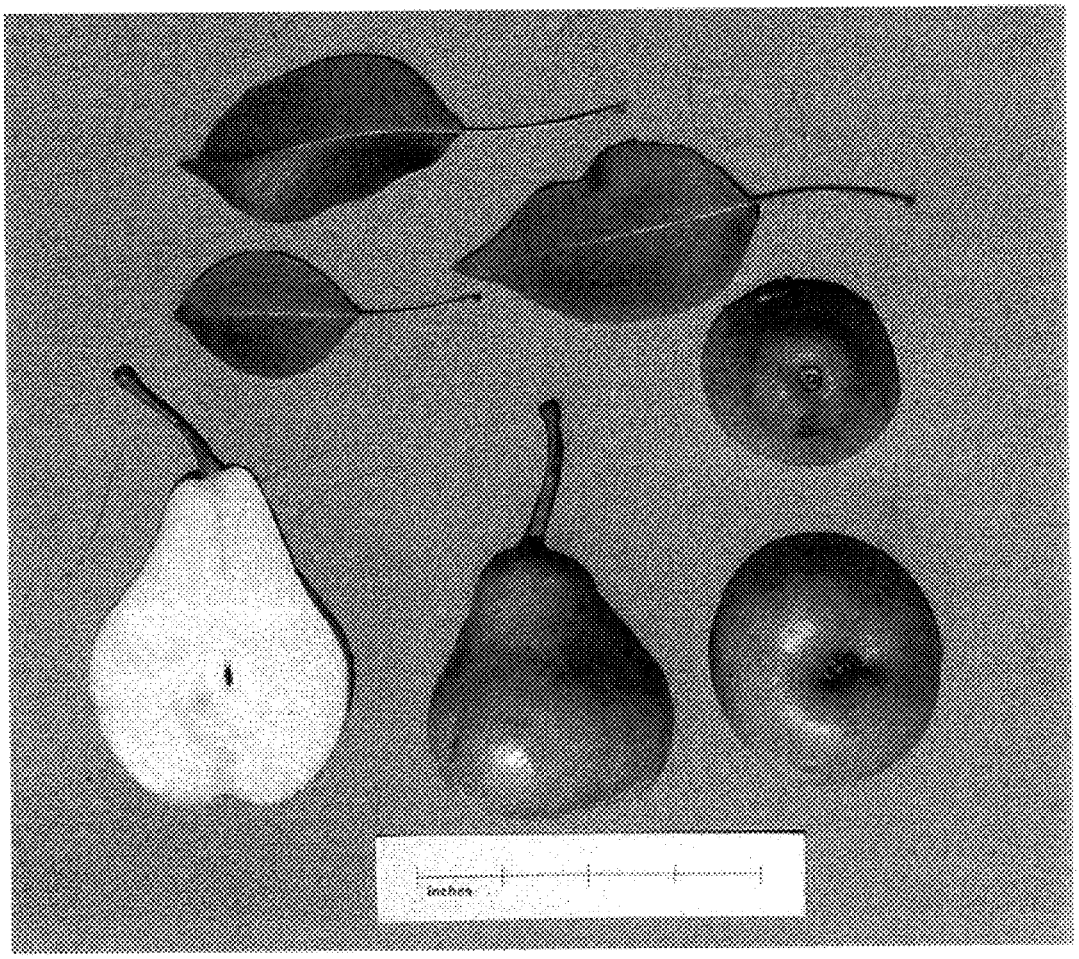
inches